United States Patent
Zhou

(10) Patent No.: US 11,351,290 B1
(45) Date of Patent: Jun. 7, 2022

(54) ABSORBABLE HIGH-STRENGTH ZINC ALLOY FOR MEDICAL IMPLANTS

(71) Applicant: Gongyao Zhou, Wilmington, DE (US)

(72) Inventor: Gongyao Zhou, Wilmington, DE (US)

(73) Assignee: ADMTECH, LLC, Wilmington, DE (US)

( * ) Notice: Subject to any disclaimer, the term of this patent is extended or adjusted under 35 U.S.C. 154(b) by 0 days.

(21) Appl. No.: 16/842,835

(22) Filed: Apr. 8, 2020

(51) Int. Cl.
- *A61L 31/14* (2006.01)
- *C22C 18/02* (2006.01)
- *A61L 31/08* (2006.01)
- *A61L 31/02* (2006.01)

(52) U.S. Cl.
CPC ........... *A61L 31/148* (2013.01); *A61L 31/022* (2013.01); *A61L 31/088* (2013.01); *C22C 18/02* (2013.01)

(58) Field of Classification Search
CPC ...................................................... C22C 18/00
See application file for complete search history.

(56) References Cited

U.S. PATENT DOCUMENTS

| | | | | |
|---|---|---|---|---|
| 3,083,096 | A * | 3/1963 | Larrieu | C22C 18/02 420/516 |
| 2017/0028107 | A1 | 2/2017 | Zhou et al. | |
| 2019/0003016 | A1 * | 1/2019 | Cao | C22C 18/00 |
| 2019/0083685 | A1 * | 3/2019 | Zhang | A61L 27/047 |
| 2019/0345585 | A1 | 11/2019 | Sherman et al. | |

FOREIGN PATENT DOCUMENTS

| | | | | |
|---|---|---|---|---|
| CN | 104328312 A * | 2/2015 | | |
| CN | 104651664 | 5/2015 | | |
| CN | 104651665 | 5/2015 | | |
| CN | 104651665 A * | 5/2015 | ............ | A61L 17/06 |
| CN | 104689378 | 6/2015 | | |
| CN | 105925847 A * | 9/2016 | | |
| CN | 104689378 B * | 4/2017 | ............ | A61L 17/00 |
| CN | 107496993 A * | 12/2017 | | |
| CN | 108277386 A * | 7/2018 | | |
| CN | 109602960 A * | 4/2019 | ............ | A61L 17/00 |
| CN | 109763004 A * | 5/2019 | | |
| WO | WO2016/145957 | 9/2016 | | |
| WO | WO-2016145957 A1 * | 9/2016 | ............ | C22C 18/00 |

OTHER PUBLICATIONS

Merriam Webster online definition of "benign" retrieved on Jun. 16, 2020 (Year: 2020).*

(Continued)

*Primary Examiner* — Keith D. Hendricks
*Assistant Examiner* — Joshua S Carpenter
(74) *Attorney, Agent, or Firm* — Joseph E. Maenner; Maenner & Associates, LLC

(57) ABSTRACT

An absorbable high-strength zinc alloy implant material includes a first tier material selected from the group consisting of Zn, Fe, and Mg, wherein Zn is in a range between about 90% and about 99% by weight and Fe and Mg is in a combined range between about 1% and about 10% by weight. The implant material can also include a second tier material being one or more element selected from the group consisting of Ag, Cu, Ce, Li, Sr, Mn, and rare earth elements, wherein the second tier material is between about 0.001% and about 10% by weight.

17 Claims, 2 Drawing Sheets

(56) References Cited

OTHER PUBLICATIONS

Wiktionary definition of "biofunctional" retrieved on Jun. 16, 2020 (Year: 2020).*
Shi, Zhang-Zhi, et al. "Effects of Ag, Cu or Ca addition on microstructure and comprehensive properties of biodegradable Zn-0.8 Mn alloy." Materials Science and Engineering: C 99 (2019): 969-978. (Year: 2019).*
Espacenet machine translation of CN-104328312-A retrieved on Jun. 17, 2020 (Year: 2015).*
Espacenet machine translation of CN-104689378-B retrieved on Nov. 15, 2020 (Year: 2017).*
Espacenet machine translation of CN-104651665-B retrieved on Nov. 15, 2020 (Year: 2017).*
Espacenet machine translation of CN-109602960-A retrieved on Nov. 15, 2020 (Year: 2019).*
Espacenet machine translation of CN-109763004-A retrieved on Apr. 2, 2021 (Year: 2019).*
Espacenet machine translation of CN-108277386-A retrieved on Apr. 2, 2021 (Year: 2018).*
Tang, Zibo, et al. "Design and characterizations of novel biodegradable Zn—Cu—Mg alloys for potential biodegradable implants." Materials & Design 117 (2017): 84-94 (Year: 2017).*
Espacenet machine translation of CN-105925847-A retrieved on Jul. 13, 21 (Year: 2016).*
Espacenet machine translation of CN-107496993-A retrieved on Jul. 13, 21 (Year: 2017).*
Shi, Zhang-Zhi t sl. "Effects of Ag, Cu, or Ga addition on microstructure and comprehensive properties of biodegradable Zn-0.8Mn alloy". Materials Science & Engineering C. vol. 99., pp. 969-978. 2019.
Yang, Lijng et al. "Influence of Mg on the mechanical properties and degradation performance of as-extruded Zn—Mg—Ca alloys: In vitro and in vivo behavior". Journal of the Mechanical Behavior of Biomedical Materials. vol. 95. pp. 220-231. 2019.
Zhou, Chao et al. "Long-term in vivo study of biodegradable Zn—Cu stent: A 2-year implantation evaluation in porcine coronary artery". Acta Biomaterialia. vol 97. pp 657-670. 2019.
Yang, Hongtao et al. "Alloying design of biodegradable zinc as promising bone implants for load-bearing applications". Nature Communications. 16 pp. 2020.

* cited by examiner

ABSORBABLE HIGH-STRENGTH ZINC ALLOY FOR MEDICAL IMPLANTS

BACKGROUND OF THE INVENTION

Field of the Invention

The present invention relates to a high-strength zinc alloy that can be used for medical implants.

Description of the Related Art

Bone screws and plates are common medical implants for fixing fractures and ligament injuries, especially for fractures close to a joint and extending to the intrajoint. Also, with an increasingly aging population, osteoporosis patients increase year by year, and accidents such as car accidents or falling down often cause comminuted fractures that need to be repaired with screws and/or plates.

Some problems involving bone screws and plates include the failure to remove non-degradable metals after the bone has healed, as well as the potential for secondary infections relating to the removal of these instruments. Meanwhile, traditional bone screws and plates have high strength, resulting in stress shielding, causing difficulty for injured bone tissue to regenerate and heal. Traditional polymer bioabsorbable bone screws and plates have relatively low strength, and can result in fracture accidents during clinical application.

Zinc is known to be fully absorbed by the body after implantation, and the strength and toughness are higher than polymers, and zinc's elasticity modulus is more similar to human bone.

Compared with biodegradable polymers such as polylactic acid, the degradation rate of Mg based alloys is considerably faster, and for medium to long term implanting, the degradation rate needs to be reduced. On the other hand, Mg and Zn based alloys are weaker than existing non-degradable metals used in implanting devices, such as titanium and stainless steel. Therefore, there is an impetus to develop methods for controlling the degradation characteristics and enhancing the mechanical performance of Mg and Zn alloys Compared with other possible biodegradable alloys of Mg, Fe and Ca, a Zn-based alloy is a more suitable bio-metal for implanted devices with a moderate degradation rate. It would be beneficial to provide a zinc alloy that provides the strength, corrosion resistance, and degradation rate required for a medical implant.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In one embodiment, the present invention provides an absorbable high-strength zinc alloy implant material that includes a first tier material selected from the group consisting of Zn, Fe, and Mg, wherein Zn is in a range between about 90% and about 99% by weight and Fe and Mg is in a combined range between about 1% and about 10% by weight.

In another embodiment, the present invention provides an absorbable high-strength zinc alloy implant material comprising a first tier material consisting of three elements, wherein all of the first tier material is biocompatible, biodegradable, bioabsorbable, and biofunctional and a second tier material, wherein the second tier material is bio-benign and at least partly biofunctional. The first tier material is between about 90% and about 99.99% by weight and the second tier material is between about 0.01% and about 10% by weight.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings.

DETAILED DESCRIPTION

Figures 1A, 1B:
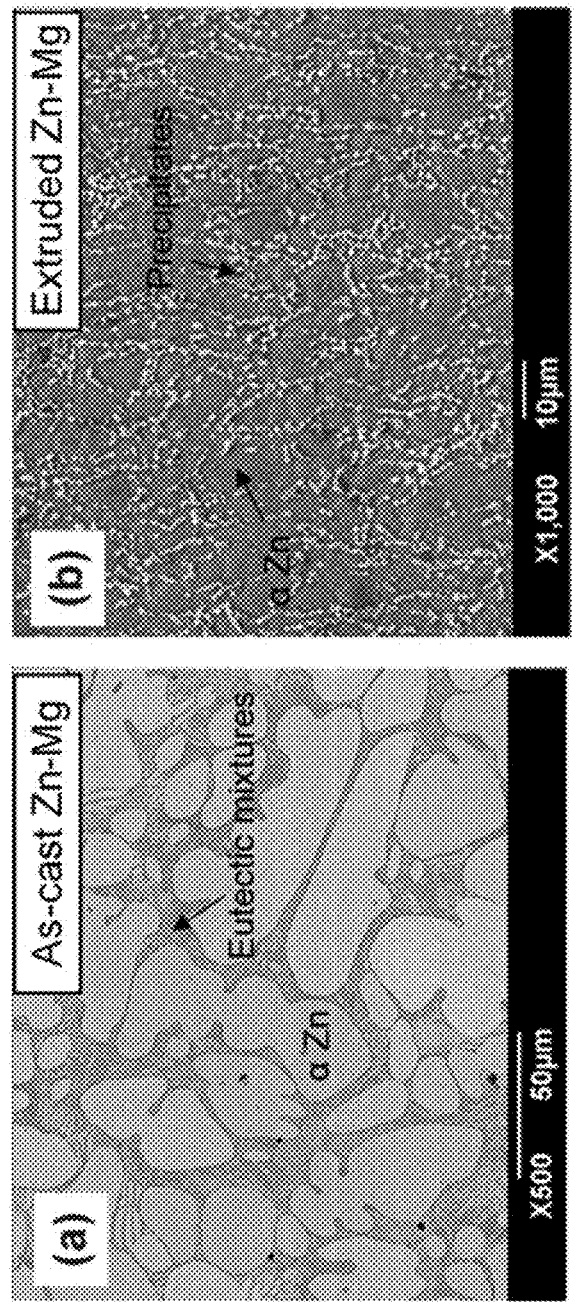
FIG. 1A is an SEM picture showing cast Zn-1Mg.
FIG. 1B is an SEM picture showing extruded Zn-1Mg.

In the drawings, like numerals indicate like elements throughout. Certain terminology is used herein for convenience only and is not to be taken as a limitation on the present invention. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

The word "about" is used herein to include a value of +/−10 percent of the numerical value modified by the word "about" and the word "generally" is used herein to mean "without regard to particulars or exceptions."

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Unless explicitly stated otherwise, each numerical value and range should be interpreted as being approximate as if the word "about" or "approximately" preceded the value of the value or range.

The use of figure numbers and/or figure reference labels in the claims is intended to identify one or more possible embodiments of the claimed subject matter in order to facilitate the interpretation of the claims. Such use is not to be construed as necessarily limiting the scope of those claims to the embodiments shown in the corresponding figures.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the present invention.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

The present invention provides zinc-based alloys for medical implant and coronary heart stent purposes. A stent manufactured by the inventive zinc-based alloy is absorbed by the patient's body. Such absorption may make vessel recovery possible when treating coronary heart disease, which is impossible when using a traditional metal stent. Because there is no permanent metal left in the body, the patient's vessel being treated by the absorbable stent may be able to move, stretch and pulse, like a new one.

Hot extrusion of Zn—Mg alloys under various processing conditions were compared with casting. Metallurgical analysis revealed significant grain size reduction, and immersion testing found that corrosion rates of Zn—Mg alloys were substantially reduced by hot extrusion. One example comparison of morphology before and after hot extrusion of Zn-1Mg is shown in FIGS. 1A and 1B. After hot extrusion, the phase size is refined by orders of magnitude. The corrosion rate in simulated body fluid (SBF) reduced from 0.28 mm/year to 0.12 mm/year. The mechanical strength increased from 140 MPa to 280 MPa. Therefore, hot extruded Zn-1Mg alloys with homogenously refined microstructure and uniform as well as slow degradation, improved mechanical properties, and good biocompatibility are believed to be an excellent candidate material for loadbearing and biodegradable implant applications.

Figure 2A:
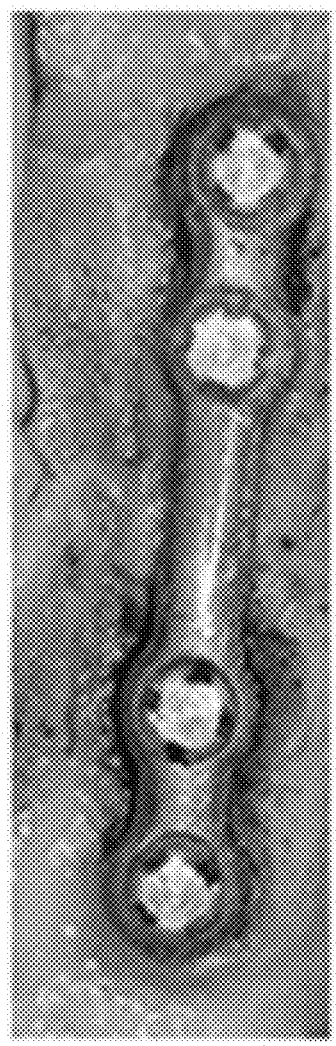
FIG. 2A is a top plan view of a plate with screws using an alloy according to the present invention at the time of implantation.
Figure 2B:
FIG. 2B is a top plan view of the plate with screws of FIG. 2A six months after implantation.

Plates and screws were manufactured from a Zn—Mg alloy and studied in vivo degradation in animal tests (dogs). The plates and screws were produced by machining of an alloy cast. The designs were taken from the common ones used by conventional titanium counterparts for fixation of mandible fractures illustrated in FIG. 2A. The weight loss of the implants in dog was monitored. After 6 months, the weight loss was about 12% for the plate and 10% for the screw. Better healing results were observed with Zn—Mg alloys; furthermore, the Zn—Mg implants can degrade in vivo. Cell cytotoxicity tests did not show formation of teratomas; nor was tissue inflation observed. Toxic substances were not detected in dog urine samples. Ingrowth of tissue was also observed at sites with degradations (FIG. 2B). These results indicate that biodegradable and resorbable Zn—Mg alloys may replace traditional non-degradable titanium alloys in implant devices.

Exemplary formulations of the inventive zinc alloy are provided below.

In order to obtain the best mechanical property and biological corrosion resistance, it is desired that the elements used have high purity: Zn purity is greater than or equal to 99.999%; Cs purity is greater than or equal to 99.99%; Mg purity is greater than or equal to 99.99%; Ca purity is greater than or equal to 99.99%; Cu purity is greater than or equal to 99.99%; the remaining elements have total impurities less than 0.1%.

The inventive alloy is constructed from elements that have been categorized in different tiers, with a first tier of elements having properties of being biocompatible, biodegradable, bioabsorbable, and biofunctional, with relatively high strength. Exemplary elements in the first tier include zinc (Zn), iron (Fe), and magnesium (Mg).

A second tier of elements has properties of being bio-benign and at least partly biofunctional. Exemplary second tier elements include silver (Ag), copper (Cu), cesium (Cs), lithium (Li), strontium (Sr), manganese (Mn), the rare earth elements, and combinations thereof.

A third tier of elements has properties of being biocompatible, biodegradable, bioabsorbable, and biofunctional, but with relatively low strength and low elongation as compared to the first tier elements. An exemplary element in the third tier is calcium (Ca).

The present invention can be used to manufacture screws, plates, and coronary heart stents. These implants have different uses and have different structural requirements. For example, a screw requires high strength (greater than 320 MPa) and low elongation (at least 6%); a plate requires moderate strength (greater than 230 MPa and high elongation (at least 20%); and a stent requires high strength (greater than 300 MPa) and high elongation (at least 25%).

In an exemplary embodiment, the first tier material is between about 90% and about 99.99% by weight of the inventive alloy and the second tier material is between about 0.01% and about 10% by weight.

In an exemplary embodiment, Zn is in a range between about 90% and about 99% by weight and Fe and Mg is in a combined range not more than 10% by weight, and can be between about 1% and about 10% by weight. Mg can be less than about 0.1% by weight and can be between about 0.01% and about 0.1% by weight, making Mg a micro-alloy. The amount of Mg in the alloy can also be 0%. Alternatively, the amount of Fe in the alloy can be between about 0.01% and about 0.1% by weight, making Fe a micro-alloy; and also Fe can be 0%.

Additionally, the second tier material can be between about 0.001% and about 10% by weight, or, alternatively, between about 0.01% and about 10% by weight.

In an exemplary alloy wherein first and second tier elements are used, the first tier material is between about 90% and about 99.99% by weight and the second tier material is between about 0.01% and about 10% by weight. Further, when the third tier material is also used, the third tier material is between about 0.1% and about 1% by weight of the alloy.

Table 1 below lists different alloy compositions according to the present invention, with the values for each composition reflecting average actual test results.

TABLE 1

| Material | Yield | UTS | Elongation | Tier |
|---|---|---|---|---|
| Zn1.5Mg0.015Fe** | 328 | 408 | 6.9 | First tier |
| Zn2Mg0.01Li** | 337 | 411 | 6.5 | First and Second tiers |
| Zn0.015Mg1.56Cu* | 326 | 336 | 40 | First and Second tiers |
| Zn0.015Mg3Cu* | 337 | 403 | 31.5 | First and Second tiers |
| Zn0.45Mg0.03Fe** | 324 | 427 | 6 | First tier |

Yield = yield strength, in MPa
UTS = Ultimate Tensile Strength, in MPa
Elongation = elongation factor of material before rupture, in percent
*Good for stents, plates and screws.
**Good for surgical screws.

Yield=yield strength, in MPa
UTS=Ultimate Tensile Strength, in MPa
Elongation=elongation factor of material before rupture, in percent
* Good for stents, plates and screws.
** Good for surgical screws.

As can be seen from Table 1, for the tested alloys, tensile strength ranges between about 336 MPa and about 427 MPa, with an elongation between about 6 percent and about 40 percent.

Table 2 below lists different compositions for a rod having a 12 mm diameter to simulate surgical plates and screws.

TABLE 2

| Materials | Yield Strength | UTS | Elongation | Tier |
|---|---|---|---|---|
| Zn0.015Mg0.6Cu** | 215 | 260 | 26 | First and Second tiers |
| Zn0.01Mg0.15Ca** | 227 | 261 | 36.5 | First and Third tiers |
| Zn0.02Mg0.9Cu** | 248 | 283 | 26.5 | First and Second tiers |
| Zn0.02Mg0.3Cu** | 192 | 250 | 36.5 | First and Second tiers |
| Zn0.015Mg1.56Cu* | 313 | 328 | 36.5 | First and Second tiers |
| Zn0.015Mg3Cu* | 337 | 403 | 31.5 | First and Second tiers |

Yield = yield strength, in MPa
UTS = Ultimate Tensile Strength, in MPa
Elongation = elongation factor of material before rupture, in percent
*Good for stents, plates, and screws.
**Good for plates.

Yield=yield strength, in MPa
UTS=Ultimate Tensile Strength, in MPa
Elongation=elongation factor of material before rupture, in percent
* Good for stents, plates, and screws.
** Good for plates.

For these alloys consisting of first tier and second tier materials, minimum tensile strength was about 250 MPa and maximum tensile strength was about 403 MPa, with a minimum elongation of about 26 percent and a maximum elongation of about 36.5 percent.

It will be further understood that various changes in the details, materials, and arrangements of the parts which have been described and illustrated in order to explain the nature of this invention may be made by those skilled in the art without departing from the scope of the invention as expressed in the following claims.

I claim:

1. An absorbable zinc alloy medical implant material consisting of:
    a first material consisting of
        Fe; and
        Mg,
            wherein Fe and Mg is in a combined range between greater than 1.0% and less than 10% by weight of the alloy;
    and
    a second material consisting of cesium, the cesium being between 0.01% and 1% by weight of the alloy, and one or more element selected from the group consisting of silver, copper, manganese, lithium, and rare earth elements, wherein the total percentage of the second material is between greater than 0.01% and less than 9% by weight of the alloy;
    and
    a remainder Zn.

2. The implant material according to claim 1, wherein the Mg is up to 0.1% by weight of the alloy.

3. The implant material according to claim 1, wherein the Fe is up to 0.1% by weight of the alloy.

4. The implant material according to claim 1, wherein the second material is between 0.1% and 9% by weight of the alloy.

5. The implant material according to claim 1, wherein the implant material has a tensile strength greater than 250 MPa.

6. The implant material according to claim 5, wherein the implant material has a tensile strength less than 500 MPa.

7. The implant material according to claim 1, wherein the implant material has an elongation factor of between about 6% and about 36%.

8. The implant material according to claim 1, wherein the implant material has a tensile strength greater than 280 MPa.

9. The implant material according to claim 8, wherein the implant material has a tensile strength less than 450 MPa.

10. The implant material according to claim 1, wherein Fe is <0.002% by weight of the alloy.

11. An absorbable zinc alloy medical implant material consisting of:
    a first material consisting of
        Fe; and
        Mg,
            wherein Fe and Mg is in a combined range between 1.0% and less than 9.88% by weight of the alloy;
    a second material consisting of cesium, the cesium being between 0.01% and 1% by weight of the alloy, and one or more element selected from the group consisting of copper, manganese, and rare earth elements, wherein the one or more element of the second material is between 0.01% and 8.89% by weight of the alloy;
    and
    a third material consisting of Ca being between 0.1% and 1% by weight of the alloy;
    and
    a remainder Zn.

12. An absorbable zinc alloy medical implant material consisting of:
    a first material consisting of Zn and Fe; and
    a second material, wherein the second material consists of cesium, the cesium being between 0.01% and 1% by weight of the alloy, copper, and silver, wherein the first material is between 90% and less than 99.99% by weight of the alloy; and wherein the second material is between greater than 0.01% and 10% by weight of the alloy.

13. The implant material according to claim 12, wherein the implant material has a tensile strength greater than 280 MPa.

14. The implant material according to claim 13, wherein the implant material has a tensile strength less than 500 MPa.

15. The implant material according to claim 12, wherein the implant material has an elongation factor of between about 6.0% and about 40%.

16. The implant material according to claim 12, wherein the implant material has a biodegradation rate between 0.15 mm/year, and about 0.12 mm/year based in simulated body fluid (SBF) immersion testing.

17. An absorbable zinc alloy medical implant material consisting of:

a first material consisting of
  Mg;
a second material consisting of cesium, the cesium being between 0.01% and 1% by weight of the alloy, and two or more elements selected from the group consisting of copper, silver, lithium, manganese, and rare earth elements, wherein the total weight of the Mg and the second material is between greater than 0.01% and 10% by weight of the alloy;
and
a remainder Zn.

* * * * *